(12) United States Patent
Tang et al.

(10) Patent No.: US 9,890,109 B2
(45) Date of Patent: Feb. 13, 2018

(54) PREPARATION OF CHEMICALS, MONOMERS AND POLYMERS FROM PLANT OILS

(71) Applicant: University of South Carolina, Columbia, SC (US)

(72) Inventors: Chuanbing Tang, Columbia, SC (US); Liang Yuan, Columbia, SC (US)

(73) Assignee: University of South Carolina, Columbia, SC (US)

( * ) Notice: Subject to any disclaimer, the term of this patent is extended or adjusted under 35 U.S.C. 154(b) by 265 days.

(21) Appl. No.: 14/940,300

(22) Filed: Nov. 13, 2015

(65) Prior Publication Data

US 2016/0137591 A1    May 19, 2016

Related U.S. Application Data

(60) Provisional application No. 62/123,320, filed on Nov. 13, 2014.

(51) Int. Cl.

| | | |
|---|---|---|
| *C07C 231/14* | (2006.01) | |
| *C08F 132/08* | (2006.01) | |
| *C08F 126/06* | (2006.01) | |
| *C07D 207/08* | (2006.01) | |
| *C08F 122/38* | (2006.01) | |
| *C07C 231/02* | (2006.01) | |
| *C07C 231/12* | (2006.01) | |
| *C08F 220/36* | (2006.01) | |
| *C08G 18/76* | (2006.01) | |
| *C08G 18/32* | (2006.01) | |

(52) U.S. Cl.
CPC .......... *C07C 231/14* (2013.01); *C07C 231/02* (2013.01); *C07C 231/12* (2013.01); *C07D 207/08* (2013.01); *C08F 220/36* (2013.01); *C08G 18/3206* (2013.01); *C08G 18/7657* (2013.01); *C08F 2438/02* (2013.01)

(58) Field of Classification Search
CPC ... C07C 231/02; C07C 231/12; C07C 231/14; C07D 207/08; C08F 220/36; C08F 2438/02; C08G 18/3206; C08G 18/7657
USPC ....................................................... 526/305
See application file for complete search history.

(56) References Cited

U.S. PATENT DOCUMENTS

2011/0269979 A1*  11/2011  Benecke .................. C07C 67/03
                                                             554/69

OTHER PUBLICATIONS

Bielawski, Christopher W., and Robert H. Grubbs. "Highly efficient ring-opening metathesis polymerization (ROMP) using new ruthenium catalysts containing N-heterocyclic carbene ligands." Angewandte Chemie International Edition 39.16 (2000): 2903-2906.
Campanella, A., et al. "Soybean oil epoxidation with hydrogen peroxide using an amorphous Ti/SiO 2 catalyst." Green Chemistry 6.7 (2004): 330-334.
Chiepari, John, et al. "Living free-radical polymerization by reversible addition—fragmentation chain transfer: the RAFT process." Macromolecules31.16 (1998): 5559-5562.
Gandini A. Polymers from renewable resources: a challenge for the future of macromolecular materials. Macromolecules 2008;41:9491-504.
Guo, Andrew, et al. "Polyols and polyurethanes from hydroformylation of soybean oil." Journal of Polymers and the Enviroment 10.1 (2002): 49-52.
King, JerryáW, RusselláL Holliday, and GaryáR List. "Hydrolysis of soybean oil, in a subcritical water flow reactor," Green Chemistry 1.6 (1999): 261-264.
Larock, Richard C., et al. "Preparation of conjugated soybean oil and other natural oils and fatty acids by homogeneous transition metal catalysis," Journal of the American Oil Chemists' Society 78.5 (2001): 447-453.
Li F, Larock RC. New soybean oil-styrene-divinylbenzene thermosetting copolymers. I. Synthesis and characterization. Journal of applied polymer science 2001;80:658-70.
Li, F., M. V. Hanson, and R. C. Larock. "Soybean oil-divinylbenzene thermosetting polymers: synthesis, structure, properties and their relationships." Polymer 42.4 (2001): 1567-1579.
Liu X, He H, Wang Y, Zhu S, Piao X. Transesterification of soybean oil to biodiesel using CaO as a solid base catalyst. Fuel 2008;87:216-21.
Luo, Qiang, et al. "Thermosetting allyl resins derived from soybean oil." Macromolecules 44.18 (2011): 7149-7157.
Matyjaszewski, Krzysztof. "Atom transfer radical polymerization (ATRP): current status and future perspectives." Macromolecules 45.10 (2012): 4015-4039.
Refvik, M. D., R. C. Larock, and Q. Tian. "Ruthenium-catalyzed metathesis of vegetable oils." Journal of the American Oil Chemists' Society 76.1 (1999): 93-98.
Williams, Charlotte K., and Marc A. Hillmyer. "Polymers from renewable resources: a perspective for a special issue of polymer reviews." Polymer Reviews 48.1 (2008): 1-10.
Xia Y, Larock RC. Vegetable oil-based polymeric materials: synthesis, properties, and applications. Green Chemistry 2010;12:1893-909.
Yu, Long, Katherine Dean, and Lin Li. "Polymer blends and composites from renewable resources." Progress in polymer science 31.6 (2006): 576-602.

\* cited by examiner

*Primary Examiner* — Ling Choi
*Assistant Examiner* — Chun-Cheng Wang
(74) *Attorney, Agent, or Firm* — Dority & Manning, PA

(57) ABSTRACT

Methods for forming a compound from a plant oil compound having a carboxylic acid group attached to an organic group are provided. The method can include performing an aminolysis reaction between the plant oil compound and a hydroxyl-containing amine compound to form a functionalized plant oil compound having an amide bond; and functionalizing the hydroxyl group to have a polyerizable vinyl group or a norbornene group to form a polyerizable plant oil compound having the amide bond and an ester bond.

13 Claims, 4 Drawing Sheets

PREPARATION OF CHEMICALS, MONOMERS AND POLYMERS FROM PLANT OILS

PRIORITY INFORMATION

The present application claims priority to U.S. Provisional Patent Application Ser. No. 62/123,320 titled "Preparation of Chemical, Monomers and Polymers from Plant Oils" of Tang, et al. filed on Nov. 13, 2014, the disclosure of which is incorporated by reference herein.

BACKGROUND

There is a growing concern about carbon source after the depletion of fossil fuels in the world of polymeric materials, as the majority of the commercialized polymer products are related to petrochemical resources, such as polystyrene, polyvinyl chloride, polypropylene, and polyethylene terephthalate. Renewable resources, such as carbohydrate, lignin, cellulose and plant oils, gain attention for the production of polymeric materials, due to their short term of reproducibility from biomass. Plant oils, mainly constituting of triglycerides, are extracted primarily from the seeds of oilseed plants. Besides the basic consumption as food, other applications are developed from this bio-renewable resource, like lubricants, biofuels, plasticizers, and construction materials. These triglycerides are also candidates as the building block of polymeric materials considering their natural abundance and inherent functionality, like the unsaturated double bond and ester groups. Challenges still present, including their heterogeneous and non-uniform structures. Plant oils have been used directly as the monomers for the preparation of cross-linked materials through the polymerization of their unsaturated alkyl chains for the applications in painting and floor coverings. Modifications of triglycerides through the unsaturated fatty acids have been attempted in the method of isomerization, epoxidation, reduction, hydroformylation, and metathesis reactions. Transformations of the triglycerides at the ester bonds have been focused on hydrolysis and transesterification to separate fatty acids from the glycerol core. Besides major applications in biodiesel manufacturing, triglyceride-derived fatty acids can be made into polymeric materials that are attractive for medical applications as they are naturally occurring and biocompatible. However, the preparation of processable polymers has not been well developed. The major challenge is the lack of both synthetic strategies to convert plant oil to polymerizable monomers, and polymerization techniques that do not affect the un-saturated double bonds in the fatty acids. This situation also limits the possibility of substituting petroleum based polymers with bio-renewable polymers in the areas of thermoplastic elastomers, thermoplastic resins, polymeric wax, varnishes, coatings, etc.

SUMMARY

Objects and advantages of the invention will be set forth in part in the following description, or may be obvious from the description, or may be learned through practice of the invention.

Methods are generally provided for forming a compound from a plant oil compound having a carboxylic acid group attached to an organic group. In one embodiment, the method includes performing an aminolysis reaction between the plant oil compound and a hydroxyl-containing amine compound to form a functionalized plant oil compound having an amide bond; and functionalizing the hydroxyl group to have a polyerizable vinyl group or a norbornene group to form a polyerizable plant oil compound having the amide bond and an ester bond.

Methods are also generally provided for forming a polymer from a plant oil compound having a carboxylic acid group attached to an organic group. In one embodiment, the method includes performing an aminolysis reaction between the plant oil compound and a double hydroxyl-containing amine compound to form a functionalized plant oil compound having an amide bond; and polymerizing the functionalized plant oil compound.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

Figure 1:
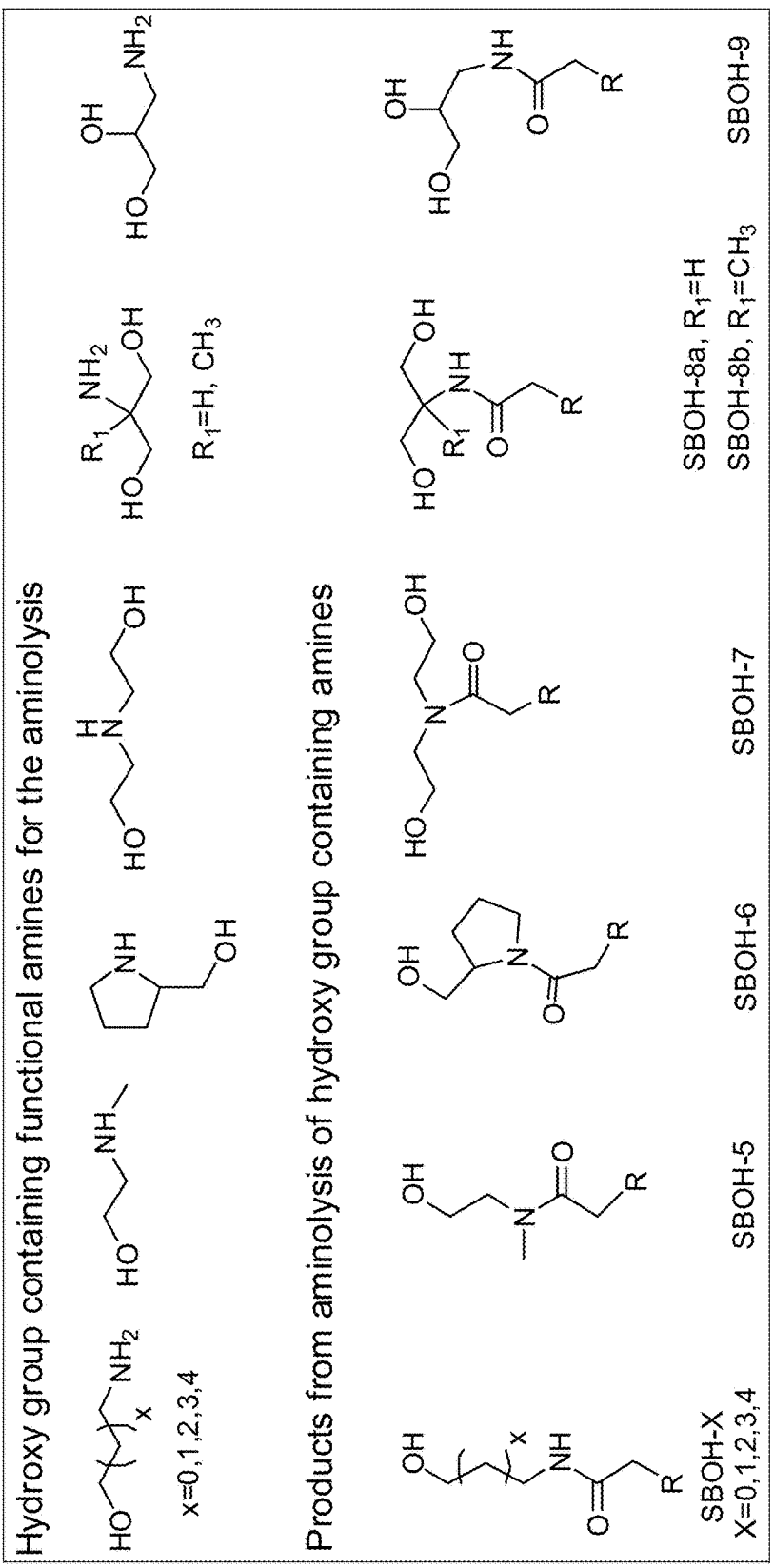
FIG. 1 shows exemplary hydroxyl-containing amines for the aminolysis and their respective products, with soybean oil used as an example of plant oil.

Repeat use of reference characters in the present specification and drawings is intended to represent the same or analogous features or elements of the present invention.

DEFINITIONS

As used herein, the term "polymer" generally includes, but is not limited to, homopolymers; copolymers, such as, for example, block, graft, random and alternating copolymers; and terpolymers; and blends and modifications thereof. Furthermore, unless otherwise specifically limited, the term "polymer" shall include all possible geometrical configurations of the material. These configurations include, but are not limited to isotactic, syndiotactic, and random symmetries.

The term "organic" is used herein to refer to a class of chemical compounds that are comprised of carbon atoms, but may also contain additional elements. For example, an "organic polymer" is a polymer that includes carbon atoms in the polymer backbone, but may also include other atoms either in the polymer backbone and/or in side chains extending from the polymer backbone (e.g., oxygen, nitrogen, sulfur, etc.). An "R group" is shorthand for an organic, including aliphatic, cyclic, and aromatic organic groups.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

A facile approach is generally provided for preparing chemicals, monomers and polymers from plant oils, in which triglycerides are major compositions. The methods provide an efficient approach to develop chemicals and monomers from triglycerides. The monomers can be polymerized through several different methods.

Additionally, polymers can be prepared by radical polymerization of plant oil derived vinyl monomers with or without petroleum-derived monomers such as styrene, methacrylate and acrylate. Resulting polymers can include poly(acrylate), poly(methacrylate), polyesters, polyurethanes and norbornene polymers, which have applications as thermoplastic elastomers, thermoplastics, shape memory polymers, etc. These polymers can be obtained through free radical polymerization, controlled radical polymerization, polycondensation, and ring opening metathesis polymerization (ROMP). Polyurethanes and polyesters can be prepared by condensation polymerization. Norbornene polymers can be prepared by ring opening metathesis polymerization. These polymers include block copolymers, random copolymers, graft copolymers and composites. Thus, the polymeric materials from the presently provided methods and monomers have the potential to replace polymers made from petroleum chemicals, thus reducing the dependence on non-renewable fossil fuels. Thus, methods are provided for forming monomers in the form of acrylate, methacrylate, multiple hydroxyl (polyol), and norbornene through aminolysis of plant oils using amino reagents or post modification of plant oil-based compounds by aminolysis.

Generally speaking, the ester groups in the triglycerides are completely converted to glycerol and functionalized fatty acids through aminolysis using primary or secondary amines.

One kind of obtained fatty acids, containing two hydroxyl groups, can react with di-isocyanates to form linear polyurethane, or can be made into polyesters through the direct esterification with diacids (sebacic acid, pimelic acid, azelaic acid, ets) or diacyl chloride (sebacoyl chloride, etc). The double bond in the alkyl chains of those di-hydroxyl groups containing compounds can be epoxidized before being incorporated into the polymers. The properties of the polyurethane or polyesters can be tuned through the choice of the co-monomers besides the diols derived from plant oil. FIG. 1 illustrates a scheme for hydroxyl containing amines for the aminolysis of triglycerides and the corresponding products.

Figure 2:
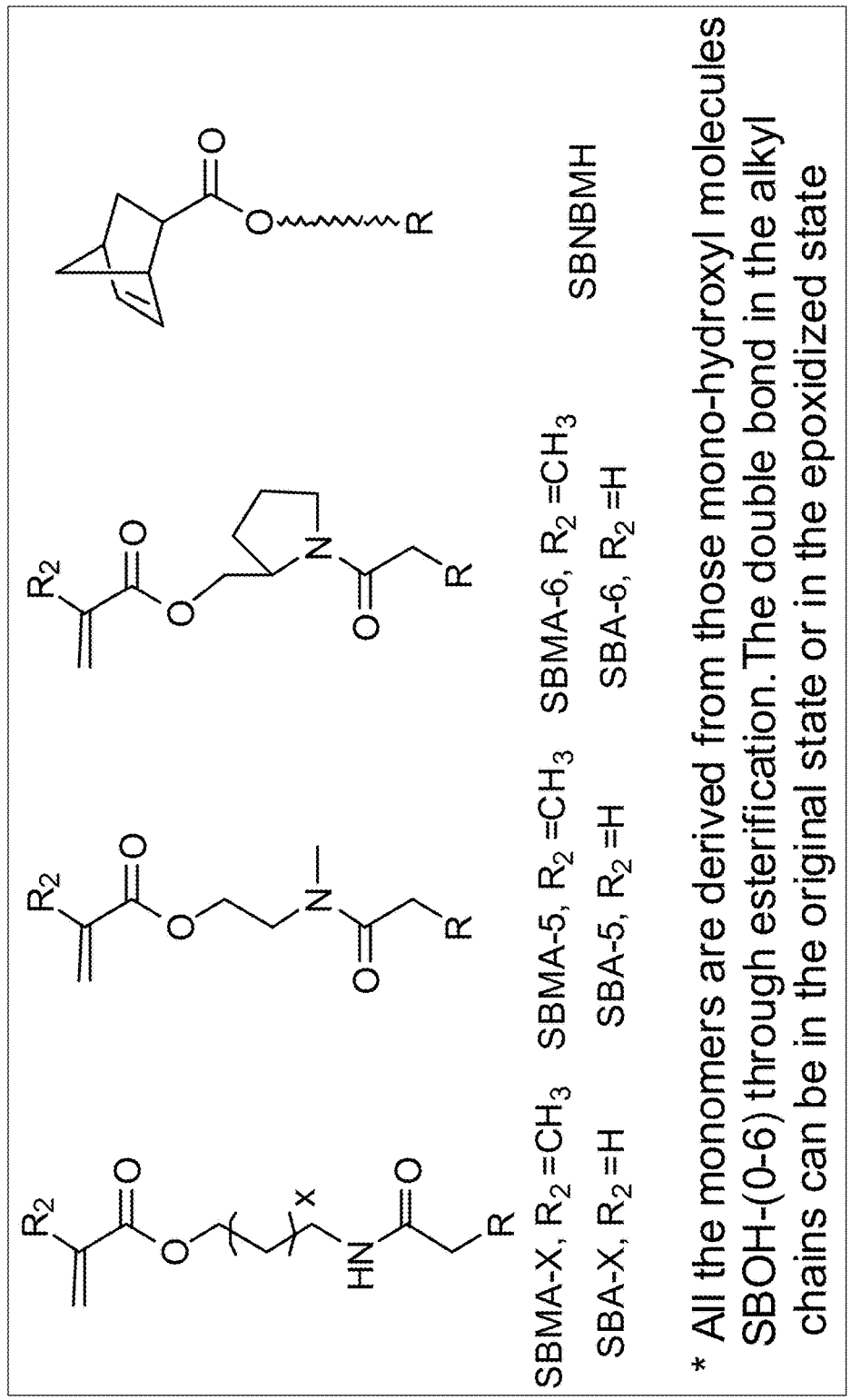
FIG. 2 shows exemplary monomers derived from the mono-hydroxyl containing products by the aminolysis.
Figure 3:
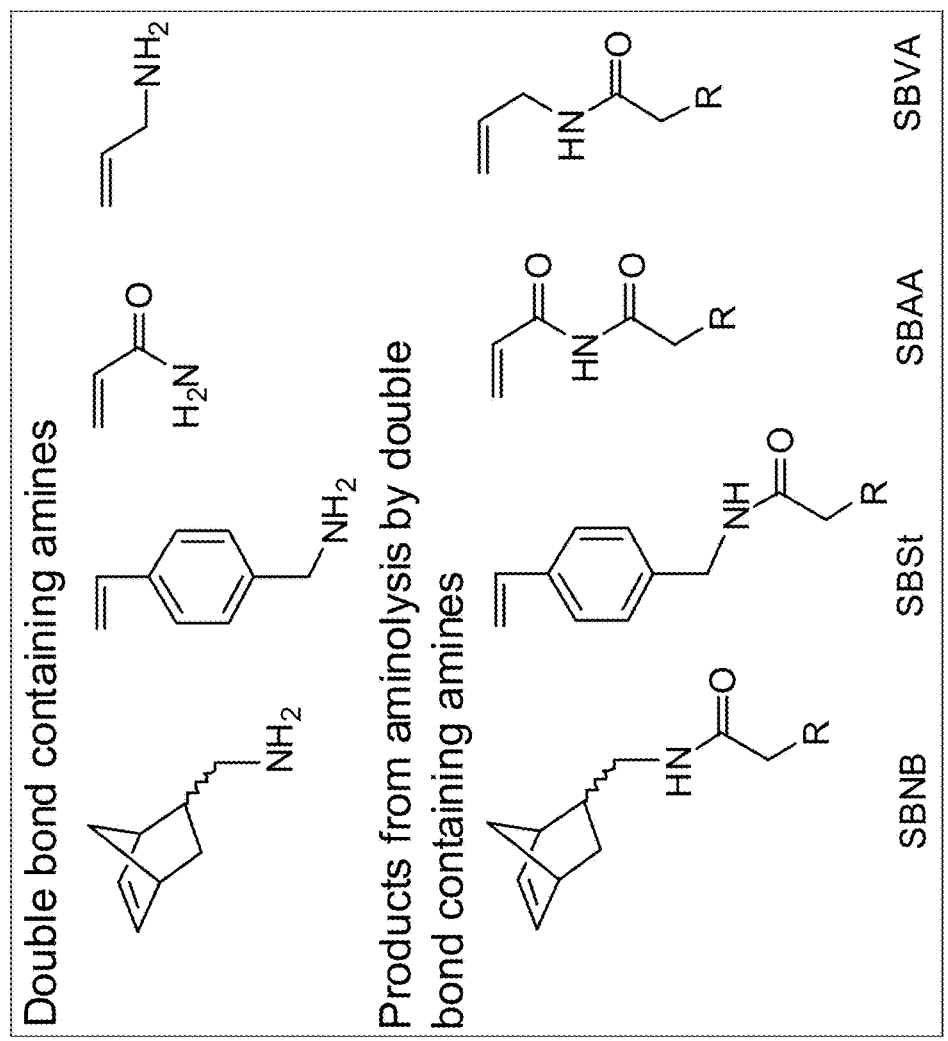
FIG. 3 shows exemplary double bond containing amines for the aminolysis of triglycerides and their corresponding respective monomers prepared.
Figure 4:
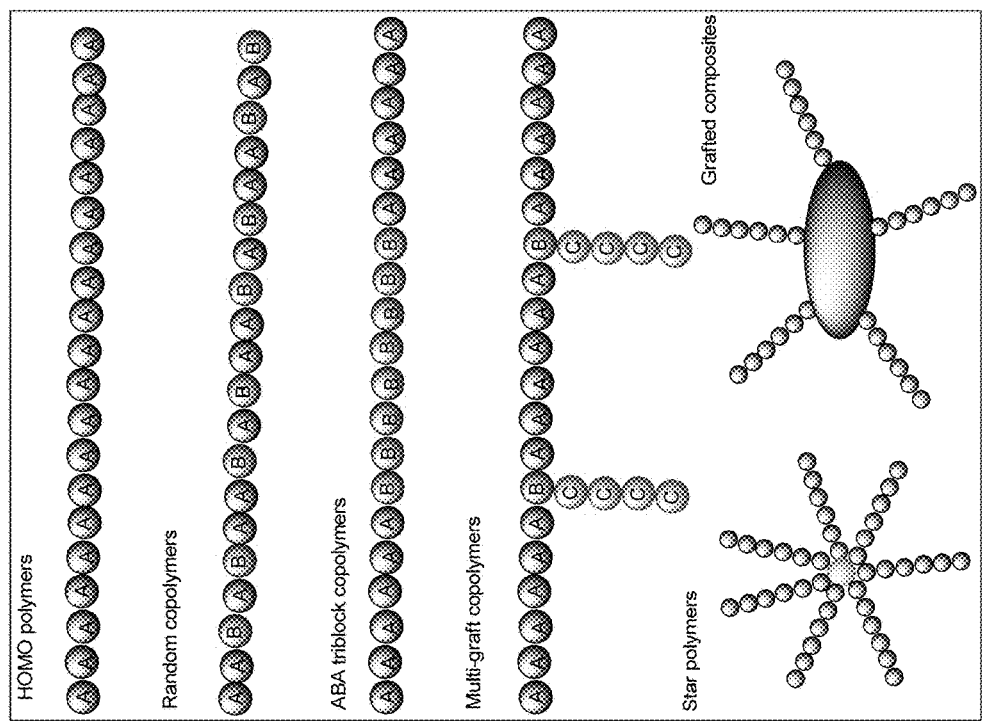
FIG. 4 shows an illustration of the structures of the polymeric materials that contain at least one polymerized monomer from triglycerides.

Other functional fatty products, which have one hydroxyl group connected to plant oil-derived fatty chain via an amide bond, can be functionalized with a polymerizable vinyl group or a norbornene group (FIG. 2). For those monomers, the unreacted double bonds can also be in the form of epoxides. The radical polymerization or ring-opening metathesis polymerization (ROMP) can be carried out after obtaining these monomers to get linear and processable (non-crosslinked) polymers. These vinyl monomers can be also subjected to controlled radical polymerizations such as atom transfer radical polymerization (ATRP), reversible addition fragmentation transfer polymerization (RAFT), which provides linear polymers with pendant fatty acid alkyl chains. Norbornene containing monomers can be polymerized through ROMP. Block copolymers can also be prepared to make thermoplastic elastomers. Other non-hydroxyl containing amines are also used for the aminolysis of triglycerides, and monomers having a polymerization end group are prepared (FIG. 3).

In certain embodiments, the presently described methods can offer one or more of the following key features: mono- and di-hydroxyl group functionalized fatty acid alkyl chains; epoxidized mono- and di-hydroxyl group containing fatty acid alkyl chains; methacrylate, acrylate and norbornene monomers derived from triglycerides fatty acids with double bonds or epoxidized double bonds in the alkyl chain; monomers containing polymerizable double bond through direct aminolysis of triglycerides with a double bond containing functional amine; triglyceride-derived fatty acid based monomers for preparation of homopolymers (e.g., polymers from free radical polymerization, polymers from controlled radical polymerization, polymers from ring opening metathesis polymerization, etc.); triglyceride based monomers for preparation of block or random copolymers (e.g., copolymers with two different components (AB diblock copolymer, AB random copolymer, ABA triblock copolymers); block copolymers with three segments (ABC triblock copolymers); graft copolymers: (i) from a polymer backbone; (ii) from macro-initiators derived from organic substrate, like lignin, cellulose, chitin, etc; (iii) from a multi-functional core to make star shaped copolymers; (iv) from a modified inorganic substrate, like silicon nanoparticles, carbon nanotubes, clay, titanium nanoparticles, gold nanoparticles, quantum dots, POSS, etc.; polymers from polycondensation of di-hydroxyl group containing fatty acid alkyl chains; segmented polymers through polycondensation, like di-hydroxyl group containing fatty acid alkyl chains based polyurethanes or polyesters); and copolymers bearing monomer besides the monomers derived from such methods described above.

In one embodiment, hydroxyl or other groups functionalized fatty acids alkyl chains can be prepared through the direct aminolysis of high oleic soybean oil by primary or secondary amines. The functional amines can contain hydroxyl group (FIG. 1) or contain double bond (FIG. 3). In another embodiment, hydroxyl groups containing products from the aminolysis of triglycerides. The double bond in the alkyl chain can be transformed into the epoxidized state, such as by meta-chloroperoxybenzoic acid (mCPBA). Then, monomers can be prepared from the mono-hydroxyl group containing products. For example, all the products that contain a hydroxyl group can be converted to (meth)acrylate monomers through the reaction with (meth)acryloyl chloride, or react with anhydrides.

Example 1

3-Amino propanol was used as an example of hydroxyl or other groups functionalized fatty acids alkyl chains prepared through the direct aminolysis of high oleic soybean oil. High oleic soybean oil (100.0 g, 0.34 mol ester bond) was put into a 250 ml round bottle flask and purged with $N_2$ at 100° C. for 1 h before cooling down to 60° C. 3-Amino propanol (34.0 g, 0.44 mol) is added via a syringe into the solution. The sodium methoxide in a methanol (30 wt %) solution, 1.5 wt % of soybean oil, is added to the mixture as a catalyst. The mixture is diluted with dichloromethane when 100% conversion is achieved. The diluted solution is washed twice with brine solution and dried over anhydrous MgSO$_4$. After filtration and evaporation of solvents, 100 g of the product is obtained in a yield of 87%. The yield from the aminolysis of different functional amine varies with the choice of the amine.

Example 2

This example shows the epoxidation of the hydroxyl group containing products from the aminolysis of triglycerides. The double bond in the alkyl chain can be transformed into the epoxidized state by meta-chloroperoxybenzoic acid (mCPBA). SBOH-5 (10 g, 0.03 mol), the aminolysis product of triglycerides by 2-(methylamino) ethanol (FIG. 1), and mCPBA (6.3 g, 0.036 mol) are dissolved in 150 ml dichloromethane (DCM) and put into an ice water bath. Sodium carbonate (4.5 g, 0.042 mol) is added into the solution. The solution is stirred for 4 hours, before aqueous solution of sodium thiosulfate is added to the mixture to reduce the remaining mCPBA. Then, sodium bicarbonate is added to the mixture to neutralize the acids in the mixture. The organic phase is washed with brine solution twice, dried with MgSO$_4$ and concentrated to get the epoxidized product.

Example 3

This example shows the preparation of (meth)acrylate monomers from mono-hydroxyl group containing product from the example-1 and the example 2. All the products that contain a hydroxyl group can be converted to (meth)acrylate monomers through the reaction with (meth)acryloyl chloride, or react with anhydrides. SBOH-5 (60.0 g, 0.177 mol) is mixed with methacrylic anhydride (27.3 g, 0.177 mol) and 4-dimethylaminopyridine (DMAP, 21.6 mg, 0.00177 mol). The reaction goes to full conversion after stirring at 60° C. overnight. Water is added to the mixture and stirs for 2 h to quench the remaining anhydride. The methacrylic acid is neutralized with NaHCO$_3$, and product SBMA-5 is dried over anhydrous MgSO$_4$. When acrylic anhydride is used instead of methacrylic anhydride, the methacrylate monomer SBMA-5 (FIG. 2) is obtained.

Example 4

The example shows free radical copolymerization of SBMA-5. A random copolymer of styrene with SBMA-5 is prepared through the initiation of azobisisobutyronitrile (AIBN). SBMA-5 (5.0 g, 12.3 mmol), styrene (1.28 g, 12.3 mmol) and 2,2'-azobisisobutyronitrile (AIBN) (20.2 mg, 0.123 mmol) is mixed in 5.0 mL of toluene. After purging with N$_2$ for 20 mins, the flask is put into an 80° C. oil bath. After 20 hours, the reaction is stopped by quenching the flask in ice-water bath. The polymer is recovered by precipitating from cold methanol and dried under vacuum.

Example 5

The example shows the preparation of polyurethane from the di-hydroxyl group containing molecule (SBOH-7, SBOH-8a, SBOH-8b, SBOH-9, as shown in FIG. 1). The reaction of SBOH-7 with methylene diphenyl diisocyanate (MDI) is illustrated to make linear polyurethane. SBOH-7 (1.0 g, 2.70 mmol) dissolved in 2.0 ml anhydrous THF, a solution of MDI (0.675 g, 2.70 mmol) in 2 ml THF is added drop by drop into the solution of SBOH-7 in ice-water bath under stirring. After finishing the addition, the reaction is stirred at 60° C. overnight. The product is obtained by evaporating the solvent under vacuum.

Example 6

This example shows the preparation of polyesters from the di-hydroxyl group containing molecules (SBOH-7, SBOH-8a, SBOH-8b, SBOH-9, as shown in FIG. 1). The reaction of SBOH-7 with sebacic acid is used to illustrate the preparation of polyesters. SBOH-7 (3.69 g, 0.01 mol), sebacic acid (2.02 g, 0.01 mol) and antimony oxide (13 mg, 0.045 mmol) are charged into a 25 ml schlenk flask and evacuated before put into an oil bath of 160° C. and reacts for two hours. The product is dissolved in DCM and antimony oxide is removed by centrifuging. Polymer product is obtained through precipitation into methanol and dried under vacuum.

Example 7

This example shows the polymerization of molecules from the direct aminolysis of soybean oil by double bond containing amines (FIG. 3). As shown in FIG. 3, the products (SBSt, SBAA, SBVA) from the aminolysis of triglycerides by (4-vinylphenyl) methanamine), allylamine, acrylamide, can be polymerized through free radical polymerization in a similar way to that described in Example 4. The product from the aminolysis of triglycerides by 5-norborene-2-methylamine (SBNB, FIG. 3), which contains a norbornene group that can be polymerized through ROMP in the presence of Grubbs 2rd catalyst. The polymerization of SBNB through ROMP is used as an example. SBNB (0.232 g, 0.6 mmol) is dissolved in 6 ml DCM, the solution is purged with N$_2$, Grubbs 2rd catalyst (8.5 mg, 0.01 mmol) in 0.5 ml DCM is added into the solution of SBNB. The reaction is stopped after 1 h by adding 3 drops of ethyl vinyl ether and stirring for 30 mins. The product is obtained by precipitating from cold methanol.

Example 8

This example shows the controlled radical polymerization of (meth)acrylate monomers derived from soybean oil (FIG. 2). The polymerization of SBMA-1 (FIG. 2) by RAFT polymerization is used as an example. SBMA-1 (3.25 g, 8.0 mmol), 4-cyano-4-(phenylcarbonothioylthio) pentanoic acid (22.4 mg, 0.08 mmol) and AIBN (1.32 mg, 0.008 mmol) are dissolved in 2.0 ml 1,4-dioxane within a 10 ml schlenk flask. Three cycles of freeze-pump-thaw are done to degas the solution. After refilling with N$_2$, the flask is put into an 80° C. oil bath and polymerized for 24 hours. The product is precipitated from cold methanol.

Example 9

This example shows the preparation of block copolymers containing monomers from soybean oil using ATRP. Ethylene bis(2-bromoisobutyrate) is used as the initiator for the polymerization of SBMA-5 with PMDETA/CuBr as the catalyst to make ABA type triblock copolymers. SBMA-5 (4.07 g, 0.01 mol), ethylene bis(2-bromoisobutyrate) (36 mg, 0.1 mmol), CuBr (28.7 mg, 0.2 mmol) and PMDETA (34.7 mg, 0.2 mmol) are charged into a 25 ml schlenk flask with 4.0 ml toluene. After degassing and protecting with N$_2$, the reaction mixture is put into 90° C. The polymer is precipitated from cold methanol when 80% conversion is achieved. The prepared polymer P(SBMA-5) is all used as the macroinitiator for the polymerization of styrene. P(SBMA-5), styrene (2.08 g, 0.02 mol), CuBr (28.7 mg, 0.2 mmol) and PMDETA (34.7 mg, 0.2 mmol) are dissolved in 4.0 ml toluene. After degassing and protecting under $N_2$, the polymerization is started by putting into 100° C. oil bath. The product is precipitated from methanol to get ABA triblock copolymer PS-b-P(SBMA-5)-b-PS. This kind of ABA triblock copolymers can also be prepared by RAFT polymerization through the application of a di-functional chain transfer agent. AB type di-block copolymers can be prepared through both polymerization strategy (ATRP and RAFT), when a mono-functional initiator or chain transfer agent is used in the polymerization.

Example 10

This example shows the preparation of graft copolymers. Generally, monomer A derived from soybean oil is copolymerized with a small ratio of another functional monomer B, which can be used to initiate the polymerization of a third monomer C. A multi-graft copolymer P(SBA-5)-co-P(HEMA-g-PLA) is prepared by the combination of free radical polymerization and ring opening polymerization (ROP). SBA-5 (3.94 g, 0.01 mol), 2-hydroxyethyl methacrylate (HEMA, 26 mg, 0.2 mmol) and AIBN (16.4 mg, 0.1 mmol) are dissolved in 4.0 ml Toluene with 0.8 ml DMF. After purging with N2 for 15 mins, the solution is put into an oil bath of 70° C. When full conversion of the monomers were achieved, D,L-lactide (2.0 g, 0.014 mol) and tin(II) 2-ethylhexanoate (28 mg 0.07 mmol) were added into the reaction mixture and the temperature is increased to 130° C. The product is recovered by precipitating from cold methanol when the conversion of lactide reaches 90%. The copolymerization of A and B can be made through free radical polymerization, RAFT, ATRP, ROMP, and polycondensation. Monomer A can be any of the monomers as developed in this invention. Monomer B and monomer C can vary with the choice of monomer A and the polymerization strategy and will not be limited monomers from triglycerides. When 2-(2-bromoisobutyryloxy)ethyl methacrylate (BEMA) is used as monomer B to copolymerize with monomer A, styrene can be selected as monomer C and polymerized by ATRP to make multi-graft copolymer P(SBA-5)-co-P(BEMA-g-PS).

Example 11

This example shows the preparation of star shaped copolymers containing monomers derived from soybean oil. Generally, a multi-functional initiator will be employed to make star polymers with homo, random or block structured arms containing monomers developed in this invention. A 3-arm structured star polymer is prepared using a RAFT agent that contains three chain transfer groups in the molecule (Sigma Aldrich, Tris(DDMAT)) with a random copolymer of SBMA-1 (FIG. 2) and styrene as the arm. SBMA-1 (4.07 g, 0.01 mol), styrene (1.04 g, 0.01 mol), Tris(DDMAT) (77 mg, 0.067 mmol), and AIBN (3.3 mg, 0.02 mmol) are dissolved in 5 ml toluene. Three cycles of freeze-pump-thaw are applied to degas the solution. After protecting under $N_2$, the flask is put into an oil bath of 80° C. After 24 hours, the reaction is stopped by quenching into liquid nitrogen. The product is recovered by precipitating from cold methanol. The initiator in this example can be changed to others which have different number of functional groups. Also, the arm can be a blocky structure instead of the random structure in the current example.

Example 12

This example demonstrates the preparation of composites materials containing polymers developed in this invention. The composites might contain inorganic materials (silicon nanoparticles, carbon nanotubes, clay, titanium nanoparticles, gold nanoparticles, quantum dots, etc) or organic nano-structured materials (cellulose, lignin, chitin, etc). The preparation strategy can be the direct blending of prepared polymers with those materials or the modification of these materials by polymerization or chemical coupling. A composite material containing lignin and polymers derived from soybean oil is used as an example. A lignin derived ATRP initiator (lignin-Br) was used for the polymerization of SBMA-5. Lignin-Br (0.04 g, 0.1 mmol —Br), SBMA-5 (4.07 g, 0.01 mol), CuBr (14.4 mg, 0.1 mmol) and PMDETA (17.3 mg, 0.01 mmol) are dissolved with 4 ml THF in a 25 ml schlenk flask. After three freeze-pump-thaw cycles, the sealed flask is refilled with $N_2$ and put into 65° C. oil bath to start the polymerization. The product is precipitated from methanol and dried under vacuum.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method for forming a compound from a plant oil compound having a carboxylic acid group attached to an organic group, the method comprising:
    performing an aminolysis reaction between the plant oil compound and a hydroxyl-containing amine compound to form a functionalized plant oil compound having an amide bond; and
    functionalizing the hydroxyl group to have a polymerizable vinyl group or a norbornene group to form a polymerizable plant oil compound having the amide bond and an ester bond.

2. The method of claim 1, wherein the hydroxyl-containing amine compound is a primary or secondary amine.

3. The method of claim 1, wherein the plant oil compound is a triglyceride.

4. The method of claim 1, wherein the hydroxyl-containing amine compound comprises an alkanolamine compound.

5. The method of claim 4, wherein the alkanolamine compound comprises methanolamine, 2-aminoethanol, 3-aminopropanol, 4-amino-1-butanol, 5-amino-1-pentanol, or a mixture thereof.

6. The method of claim 1, wherein the hydroxyl-containing amine compound comprises N-methylethanolamine, 2-pyrrolidinemethanol, or a mixture thereof.

7. The method of claim 1, wherein the hydroxyl group is functionalized to have a polymerizable vinyl group by reacting the functionalized plant oil compound with a (meth)acryloyl halide.

8. The method as in claim 7, further comprising:
    polymerizing the polymerizable vinyl group.

9. The method of claim 1, wherein the hydroxyl group is functionalized to have a norbornene group by reacting the functionalized plant oil compound with 5-norbornene-2-methylamine.

10. The method as in claim 9, further comprising:
polymerizing the norbornene group.

11. A method for forming a polymer from a plant oil compound having a carboxylic acid group attached to an organic group, the method comprising:
   performing an aminolysis reaction between the plant oil compound and a double hydroxyl-containing amine compound to form a functionalized plant oil compound having an amide bond; and
   polymerizing the functionalized plant oil compound.

12. The method of claim 11, wherein the amino group is a primary or secondary amine, and wherein the reaction plant oil compound having a carboxylic acid comprises a fatty acid.

13. The method of claim 11, wherein the plant oil compound is derived from a triglyceride through aminolysis.

* * * * *